United States Patent
Bernard

(10) Patent No.: US 10,096,106 B2
(45) Date of Patent: Oct. 9, 2018

(54) COMBINED MEDICAL IMAGING

(71) Applicant: General Electric Company, Schenectady, NY (US)

(72) Inventor: Sylvain Bernard, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/348,559

(22) Filed: Nov. 10, 2016

(65) Prior Publication Data
US 2018/0130201 A1    May 10, 2018

(51) Int. Cl.
| | |
|---|---|
| G06K 9/00 | (2006.01) |
| G06T 7/00 | (2017.01) |
| A61B 6/02 | (2006.01) |
| A61B 6/00 | (2006.01) |
| G06T 11/00 | (2006.01) |
| A61B 5/05 | (2006.01) |

(52) U.S. Cl.
CPC ............ *G06T 7/0012* (2013.01); *A61B 6/025* (2013.01); *A61B 6/466* (2013.01); *A61B 6/482* (2013.01); *A61B 6/502* (2013.01); *A61B 6/5235* (2013.01); *G06T 11/003* (2013.01); *G06T 2207/10116* (2013.01); *G06T 2207/30068* (2013.01)

(58) Field of Classification Search
USPC ........ 382/100, 128–134, 154–155, 162, 168, 382/173, 181, 199, 209, 220, 224, 232, 382/254, 274–276, 285–294, 305, 312; 600/425; 378/4, 21; 128/132
See application file for complete search history.

(56) References Cited

U.S. PATENT DOCUMENTS

| | | | | |
|---|---|---|---|---|
| 7,218,766 | B2* | 5/2007 | Eberhard | A61B 6/463 128/922 |
| 7,653,229 | B2* | 1/2010 | Kaufhold | G06T 11/006 378/21 |
| 7,881,428 | B2 | 2/2011 | Jing et al. | |

(Continued)

FOREIGN PATENT DOCUMENTS

| | | |
|---|---|---|
| EP | 1351192 A1 | 10/2003 |
| EP | 1792569 A2 | 6/2007 |

(Continued)

OTHER PUBLICATIONS

Kalke et al., "Sinogram Interpolation Method for Sparse-Angle Tomography", Applied Mathematics, Feb. 2014, vol. 5, pp. 423-441.

(Continued)

*Primary Examiner* — Seyed Azarian

(57) ABSTRACT

Systems and methods of imaging an organ of a patient include obtaining a plurality of two-dimensional (2D) tomosynthesis projection images of the organ. An x-ray image of the organ is obtained. A three-dimensional (3D) volume of the organ is reconstructed from the plurality of projection images and the x-ray image. A synthetic 2D image of the organ is generated from the plurality of projection images and the x-ray image. The x-ray image is mapped to the 3D volume. A user selection of an object of interest in the x-ray image or the synthetic 2D image is received. A plane through the 3D volume that crosses the selected object of interest is identified and displayed.

27 Claims, 3 Drawing Sheets

(56) References Cited

U.S. PATENT DOCUMENTS

| | | |
|---|---|---|
| 8,452,379 B2 | 5/2013 | Defreitas et al. |
| 8,565,374 B2 | 10/2013 | Defreitas et al. |
| 8,824,761 B2 | 9/2014 | Palma et al. |
| 8,831,171 B2 | 9/2014 | Jing et al. |
| 2008/0045833 A1 | 2/2008 | Defreitas et al. |
| 2009/0080765 A1* | 3/2009 | Bernard ................ G06T 11/006 382/154 |
| 2011/0150178 A1 | 6/2011 | Bernard et al. |
| 2012/0121064 A1 | 5/2012 | Bernard |
| 2014/0140604 A1* | 5/2014 | Carton .................. A61B 6/481 382/132 |
| 2015/0110239 A1 | 4/2015 | Muller et al. |
| 2015/0182181 A1* | 7/2015 | Ruth .................... G06T 11/006 600/425 |
| 2015/0327826 A1 | 11/2015 | Smith et al. |
| 2016/0189376 A1 | 6/2016 | Bernard et al. |

FOREIGN PATENT DOCUMENTS

| | | |
|---|---|---|
| FR | 959374 A | 3/1950 |
| FR | 2905256 A | 3/2008 |
| FR | 2 967 520 B1 | 12/2012 |
| GB | 2533801 A | 7/2016 |
| JP | 2015506794 A1 | 3/2015 |
| WO | 01/80184 | 10/2001 |

OTHER PUBLICATIONS

GE Healthcare Brochure—SenoClaire 3D Breast Tomosynthesis, 2014.

Extended European Search Report and Opinion issued in connection with corresponding EP Application No. 17194802.9 dated Mar. 16, 2018.

* cited by examiner

COMBINED MEDICAL IMAGING

BACKGROUND

The present disclosure relates to the field of acquisition, processing, and display of tomosynthesis images and radiography images of an organ. More specifically, the present disclosure relates to a system and method for combined acquisition of tomosynthesis projection images and X-ray images and processing and display of combined imaging from these acquisitions.

Radiography is generally used for seeking abnormalities in an object of interest. A radiography image represents a projection of an object, for example an organ of a patient. In a more specific, nonlimiting, example, the organ is a breast and the images are mammographic images. Mammography has been used for decades for screening and diagnosing breast cancer. The radiography image is generally obtained by placing the object between a source emitting X-rays and a detector of X-rays, so that the X-rays attain the detector having crossed the object. The radiography image is then constructed from data provided by the detector and represents the object projected on the detector in the direction of the X-rays.

In the case of mammography, an experienced radiologist may distinguish radiological signs indicating a potential problem, for example microcalcification, masses, or other opacities. However, in a 2D projection image, super position of the tissues may hide lesions, but in no case is their actual position known in the object of interest, the practitioner not having any information on the position of the radiological sign in the projection direction.

Tomosynthesis is used in order to address these problems. In tomosynthesis a 3D representation of an organ may be obtained as a series of successive slices. The slices are reconstructed from projections of the object of interest under various angles. To do this, the object of interest is generally placed between a source emitting X-rays and a detector of X-rays. The source and/or the detector are mobile, so that the direction of projection of the object on the detector may vary (for example over an angular range of 30°). Several projections of the object of interest are thereby obtained under different angles, from which a three-dimensional representation of the object may be reconstructed, generally by a reconstruction method, for example as those known to one skilled in the art.

For each projection, the radiation doses of the X-rays are naturally less than those used for standard mammography. For example, by noting as D the radiation dose by standard mammography, and as N the number of projections used for tomosynthesis, the radiation dose used for each projection is generally of the order of D/N.

While both standard mammography and tomosynthesis are currently used by radiologists, each technique has advantages. Standard mammography forms better than tomosynthesis in imaging microcalcifications. This may be due to the higher energy and dose used to obtain any individual standard mammography image and also that the reconstruction process in tomosynthesis tends to blur edges of the already small calcifications. Tomosynthesis is superior in imaging of spiculated masses as the reconstruction in the tomosynthesis properly locates the mass within the organ as well as super position and back projection errors from objects of interest within the organ.

While radiologists may acquire both standard mammography and tomosynthesis images to leverage the advantages of each technique, these imaging processes are typically performed sequentially with the radiologist switching between the imaging techniques.

Rather, solutions that combine the acquisition, processing, and display of digital radiography and tomosynthesis can provide enhanced imaging solutions at the same or reduced radiation dose.

BRIEF DISCLOSURE

An exemplary embodiment of a method of imaging an organ of a patient includes obtaining a plurality of two-dimensional (2D) projection images of the organ by rotating an X-ray emitter to a plurality of orientations relative to the organ and emitting a first level of X-ray energization from the emitter for each projection image of the plurality of projection images. An X-ray image of the organ is obtained with a second level of X-ray energization. The second level of X-ray energization is often greater than the first level of X-ray energization. A three-dimensional (3D) volume of the organ is reconstructed from the plurality of projection images. The X-ray image is mapped to the 3D volume. The X-ray image is presented in a graphical user interface (GUI) presented on a graphical display. A user selection of an object of interest in the X-ray image is received. A plane through the 3D volume that crosses the selected object of interest is identified. The identified plane is presented on the graphical display.

In another embodiment, a three-dimensional (3D) volume along with a Synthetic 2D image of the organ are reconstructed from the plurality of projection images and the X-ray image. The X-ray image is enhanced with pixel information from the 2D projection images and/or with areas from the 3D volume. The X-ray image is mapped to the 3D volume. The X-ray image is presented in a graphical user interface (GUI) presented on a graphical display. A user selection of an object of interest in the X-ray image is received. A plane through the 3D volume that crosses the selected object of interest is identified. The identified plane is presented on the graphical display.

An exemplary embodiment of a system of medical imaging includes an X-ray emitter capable of producing X-rays at a first energization level and a second energization level. The second energization level is often greater than the first energization level. The X-ray emitter is rotatable to a plurality of orientations. A processor is operably connected to the X-ray emitter and the X-ray detector. The processor operates the X-ray emitter and X-ray detector to rotate about an organ to be imaged and obtain a plurality of 2D projection images of the organ. The processor operates the X-ray emitter and X-ray detector to acquire an X-ray image of the organ at the second energization level. A graphical display is operably connected to the processor. The graphical display is operated by the processor to present the X-ray image of the organ in a graphical user interface presented on the graphical display. The processor reconstructs a 3D volume of the organ from the plurality of projection images. The processor maps the X-ray image to the 3D volume. Upon receiving a user selection of an object of interest in the X-ray image presented in the GUI on the graphical display, the processor identifies a plane through the 3D volume that crosses the selected object of interest based upon a map of the X-ray image to the 3D volume. The processor operates the graphical display to present the identified plane.

DETAILED DISCLOSURE

Figure 1:
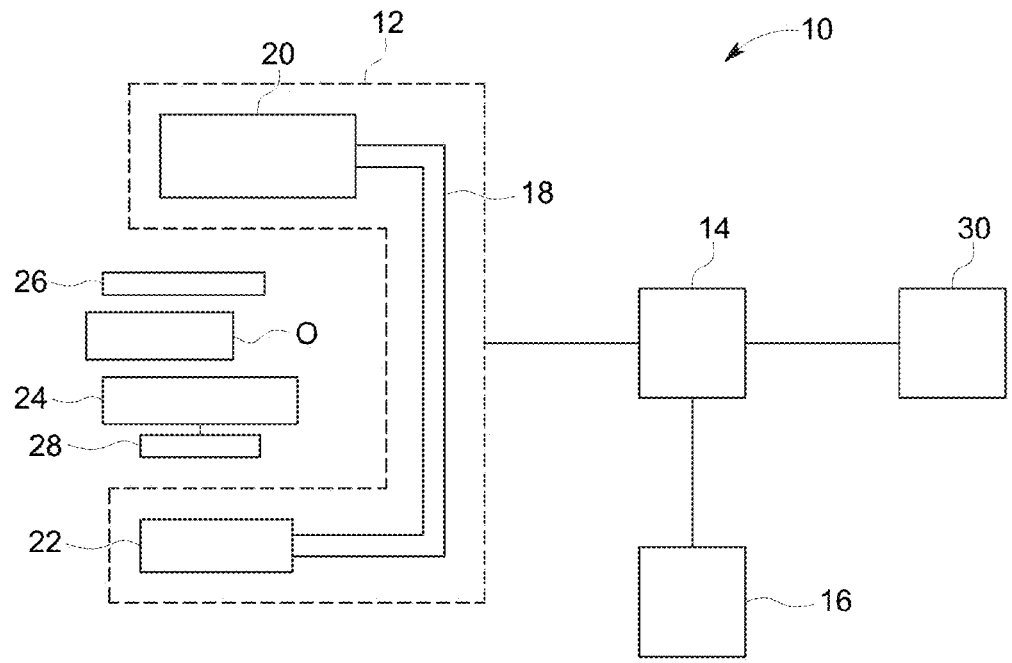
FIG. 1 is a schematic diagram of a medical imaging system.

FIG. 1 is a schematic diagram of an exemplary embodiment of a medical imaging system 10. The system 10 includes an image acquisition unit 12, an image processing unit 14, and a graphical display 16. It will be recognized that while the embodiment of the system 10 as depicted herein in FIG. 1 shows a single image acquisition unit 12, that in other embodiments will be recognized by a person of ordinary skill in the art, additional image acquisition units may be used. In one exemplary embodiment, separate image acquisition units may be used to acquire tomographic projection images and another image acquisition unit to acquire X-ray images.

In the present application the example of mammography will be used herein although it will be recognized that other radiographic application and imaging of other organs and organ systems may be performed using the systems and methods as disclosed herein.

The image acquisition unit 12 includes a C-arm 18. The C-arm 18 includes, at opposing ends, an X-ray emitter 20 and an X-ray detector 22.

The system 10 includes a lower support 24 and compression support 26. The organ to be imaged, for example a breast of a patient is placed on the lower support 24. The lower support 24 holds the organ in a relative axial alignment with the C-arm 18 between the X-ray emitter 20 and the X-ray detector 22. A compression support 26 is lowered to compress the organ between the lower support 24 and the compression support 26. compression of the organ improves imaging quality. In acquiring radiographic images of the organ, the X-ray emitter 20 is operated to produce X-rays which are projected in the direction of the organ O. The X-rays pass through the organ O to the detector 22. In an exemplary embodiment, the imaging system 10 can also be provided with an anti-diffusion grid 28. The anti-diffusion grid 28 can include a plurality of opaque components arranged parallel to one another, in a direction parallel to the motion of the C-arm 18. Such anti-diffusion grids are known to limit the impact of the spread of emitted X-rays within the patient's body. The C-arm 18 is exemplarily coaxially aligned with the organ O, for example in the compressed position exemplarily held between the lower support 24 and the compression support 26. The C-arm 18 is operable to rotate about the organ O held in this position. While the system 10 depicted in FIG. 1 shows the X-ray detector 22 being rotatable in conjunction with the emitter 20, such that the emitter 20 and the detector 22 are maintained in alignment, it will be recognized that in additional embodiments of medical imaging systems, the detector 22 may be held in a fixed position relative to the organ O, for example, by locating the X-ray detector 22 in the lower support 24.

Figure 2:
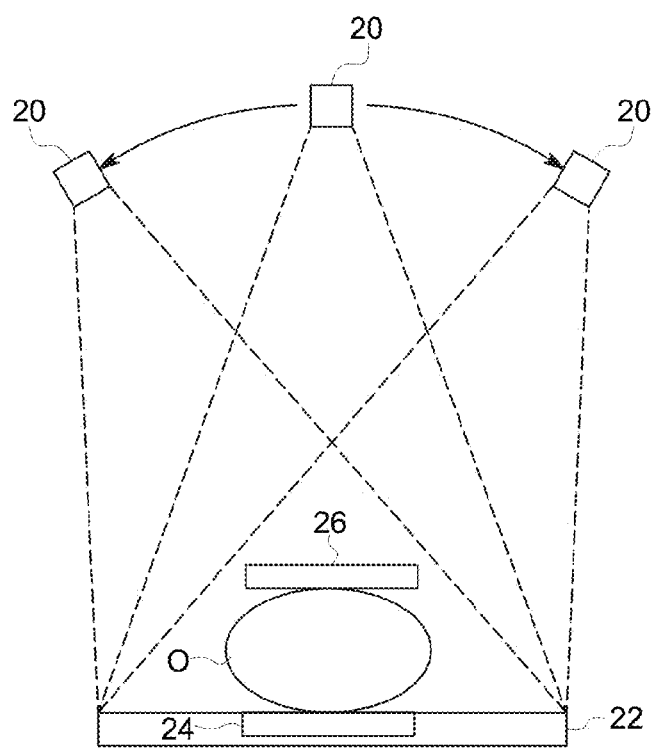
FIG. 2 depicts rotation of the imaging apparatus about an object to acquire radiographic images.

FIG. 2 depicts exemplary movement of the emitter 20 relative to the organ O. As the emitter 20 is rotated about the organ, the emitter may further include beam shaping (not depicted) to direct the X-rays through the organ to the detector 22. In the embodiment depicted the detector 22 is integrated into the lower support 24. In either embodiment, the emitter is rotatable about the organ O to a plurality of orientations with respect to the organ O. In an exemplary, and non-limiting embodiment, the emitter 20 may rotate through a total arc of 30° relative to the organ O or may rotate 30° in each direction (clockwise and counterclockwise) relative to the organ O. It will be recognized that these arcs of rotation are merely exemplary and not intended to be limiting on the scope of the angulation which may be used in embodiments.

It will be recognized that the emitter 20 is positionable to a position or orthogonal to one or both of the organ O and the detector 22. In this orthogonal or center position, a full field digital mammography (FFDM) may be acquired, particularly in an embodiment in which a single emitter and detector are used to acquire both the FFDM image as well as the digital breast tomosynthesis (DBT) projection images. The DBT projection images are acquired at various angles of the emitter 20 about the organ O. Exemplarily using the imaging system 10 as described herein, there are various imaging work flows which may be used in embodiment disclosed in the present application. In one exemplary embodiment the FFDM image is obtained at the position orthogonal to the organ and the DBT projection images are acquired at various angles relative to the organ O, including a DBT projection image acquired at the emitter position orthogonal to the organ. During reconstruction as described in further detail herein, all of the DBT projection images and the FFDM image are used to reconstruct the 3D volume of the organ.

In a next exemplary embodiment, the DBT projection images are acquired at various angles of the emitter 20 relative to the organ. However, a DBT projection image is not acquired at the position of the emitter orthogonal to the organ and instead only an FFDM image is acquired. The 3D volume of the organ is reconstructed using both the DBT projection images as well as the FFDM image.

In another exemplary embodiment, the DBT projection images are acquired at various angles of the emitter relative to the organ, including at a position orthogonal to the organ. An FFDM image is acquired orthogonally to the organ. During reconstruction of the 3D volume of the organ, the FFDM image replaces the DBT projection image acquired with the emitter orthogonal to the organ. A still further exemplary embodiment, DBT projection images are acquired about the organ at various angle of the emitter relative to the organ. As previously noted, the level of energization of each individual DBT projection image is typically lower than that of the X-ray energy level at which the FFDM is acquired. In this further exemplary embodiment, a dynamic energization is used throughout the acquisition of the DBT projection images such that the DBT projection images at the greatest angles relative to the position orthogonal to the organ have the lowest X-ray energization and the X-ray energization used at acquisition of each subsequent DBT projection image as the angulation of the emitter relative to the organ approaches the orthogonal increases until the DBT projection image acquired orthogonal to the organ approaches or is equal to the X-ray energy at which an FFDM image is acquired.

Referring back to FIG. 1, the image processing unit 14 may further be connected to a memory unit 30 which may exemplarily be a non-transient computer readable medium. The memory unit 30 may be located inside or outside the processor 14. The processor 14 may operate to read and/or write information from/to the memory unit 30. The memory unit 30 may exemplarily be a hard disk or SSD or any other re-right removal storage medium (e.g. USB flash drives, memory cards, etc.). The memory unit 30 may be a ROM/ RAM memory of the processor 14, flash memory, and/or memory on a remotely located server. The memory may further be programmed with computer readable code embodying one or more programs, routines, or subroutines which is accessible by the processor 14 and executable by the processor 14 to carry out the acquisition unit control, image processing, and display functions and operations as disclosed in further detail herein.

Figure 3:
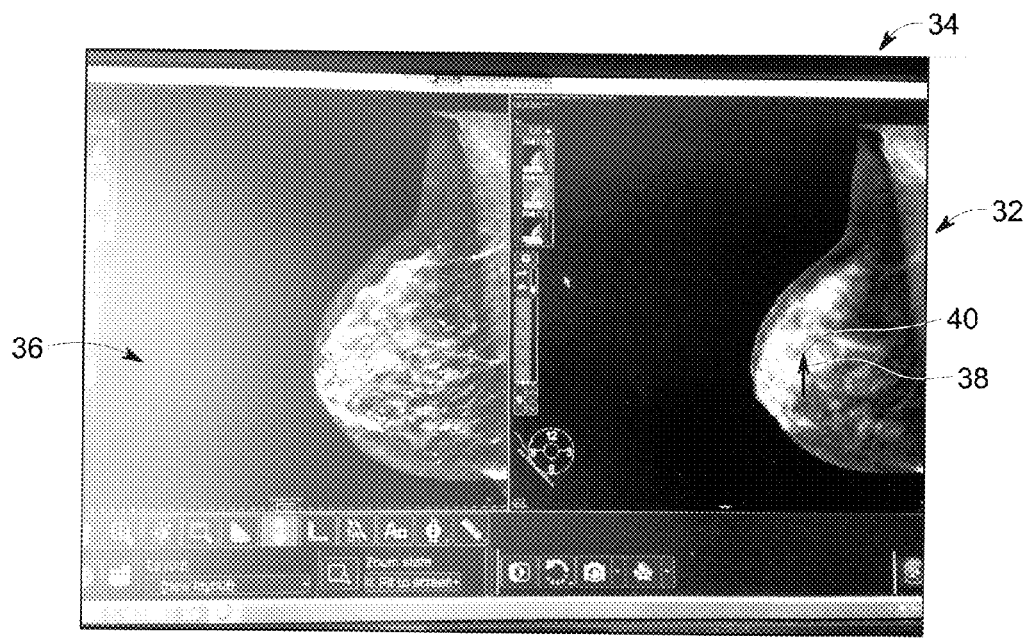
FIG. 3 is an exemplary embodiment of a screen shot depicting both a FFDM image and a tomographic image.

FIG. 3 is a flow chart that depicts an exemplary embodiment of a method 100 of medical imaging of an organ. It will be recognized that embodiments of the method 100 may be carried out by the system as depicted in FIGS. 1 and 2, as well as other embodiments of medical imaging systems as would be recognized by a person of ordinary skill in the art in view of the present disclosure.

The method 100 begins at 102 where DBT projection images are obtained. The DBT projections images are obtained at 102 in the manner as described above by rotating the emitter relative to the organ to be imaged and capturing a plurality of radiographic projection images with X-rays at a first X-ray energization level. At 104 the system is operated to obtain at least one FFDM image. As described above, the FFDM image is obtained by an emitter emitting X-rays of a second X-ray energization level wherein the second energization level could be greater than the first energization level. The FFDM image is obtained with an emitter at a position orthogonal to the organ to be imaged. For example, the FFDM image is a cranial-caudal image of the organ, exemplarily a breast.

At 106 a 3D volume of the organ to be imaged is reconstructed. In an exemplary embodiment, the 3D reconstructed volume is reconstructed using a filtered back projection (FBP) reconstruction technique or an iterative reconstruction technique, both of which are known by persons of ordinary skill in the art. The 3D volume may be exemplarily reconstructed from only the DBT projection images, while in still further embodiments, as described herein, the 3D volume of the organ to be imaged is reconstructed using the obtained FFDM image as well as at least some of the DBT projection images, for example in the reconstruction examples provided above.

At 108 the FFDM image is mapped to the reconstructed 3D volume. This navigational map created at 108 facilitates image display, review, and analysis work flows enabled by the systems and methods as disclosed herein.

The navigational map created at 108 exemplarily created by first creating a synthetic 2D image from the reconstructed 3D volume. Because the DBT projection images and the FFDM image are acquired during the same compression of the organ and imaging session, which in embodiments uses the same emitter and detector to acquire both the DBT projection image and the FFDM image, the synthetic 2D image obtained from the 3D reconstruction positionally matches the FFDM image. The navigational map may consist of an identifier of the reconstruction slice in which a maximum intensity voxel is found along the ray from the source to each pixel (also known as reprojection operator). These identifiers may be stored in the computer readable memory. These identifiers connect each pixel of the FFDM and/or synthetic 2D image to the associated reconstruction slice from which this pixel stems. In an exemplary embodiment, the navigation map is stored into a DICOM header of the x-ray image and/or of the synthetic 2D image.

In an optional and exemplary embodiment, the FFDM image may be registered to the reconstructed 3D tomosynthesis volume. In an embodiment, since the FFDM image and the 2D projection images are acquired under a single compression of the breast, the registration process may be simplified due to greater correspondence between the images. In other embodiments, the navigational map may be used to register the FFDM image to the reconstructed 3D tomosynthesis volume.

In an exemplary embodiment, the x-ray image is enhanced with information extracted from the 3D volume and combined into the FFDM image. The extraction process can be automatically performed by a 3D CAD system or manually by an operator. The mapping is then modified to include the z-position of the extracted areas at the corresponding (x,y) location in the FFDM image. A transformation involving a magnification factor might be required to compute the (x,y) position from the volume to the FFDM image.

Next, at 110 the FFDM image is presented on the graphical display. This is exemplarily depicted by FFDM image 32 shown in the exemplary embodiment of a graphical user interface (GUI) 34 presented on a graphical display 16 as depicted in FIG. 3. While FIG. 3 further depicts an exemplary presentation of a synthetic 2D image 36 as described in further detail herein, alternatively, the reconstructed 3D volume may be initially presented in this portion of the GUI 34.

Figure 4:
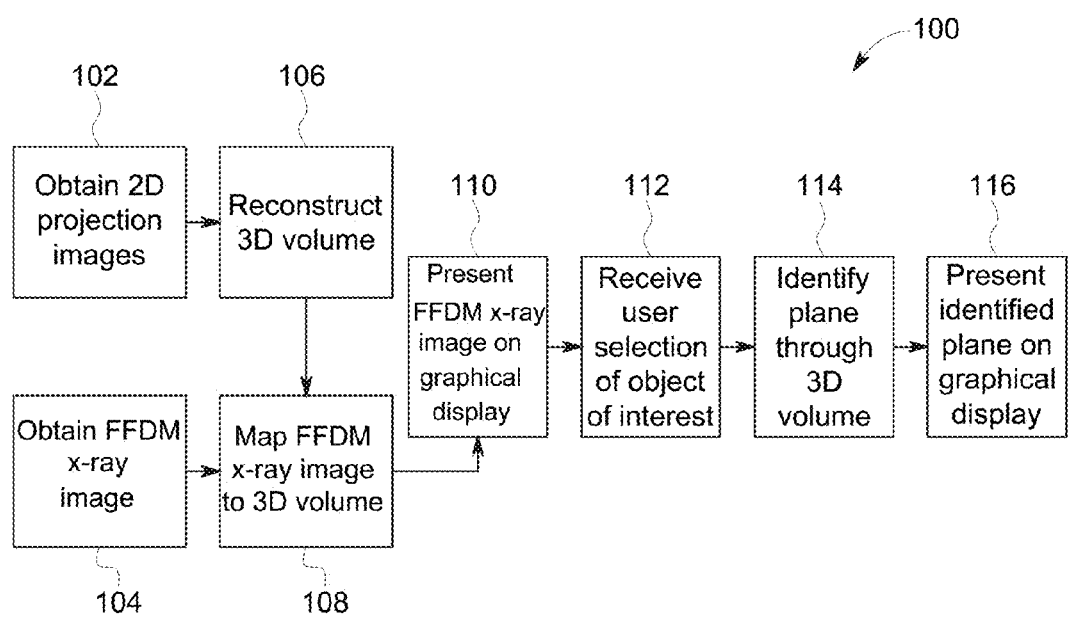
FIG. 4 is a flow chart that depicts an exemplary embodiment of a method of imaging an organ of a patient.

Referring back to FIG. 4 at 112 the system may receive a user selection of an object of interest within the FFDM image. This is exemplarily depicted in FIG. 3 by cursor 38 which is exemplarily positioned upon an object of interest 40 in the FFDM image. In an exemplary embodiment, the object of interest 40 may be a calcification, microcalcification, or a lesion, while it will be recognized that other forms of objects of interest may be selected by a user reviewing the FFDM image 32.

Next, at 114 a plane through the 3D volume is identified that includes the object of interest selected by the user. The navigation map created at 108 is used to locate the object of interest 40 selected in the FFDM image 32 in the reconstructed 3D volume and a plane through the object of interest in the 3D reconstruction volume is identified. In embodiments, the user may further select a thickness of the plane through the 3D reconstructed volume or other embodiments may use a default plane width.

Figure 5:
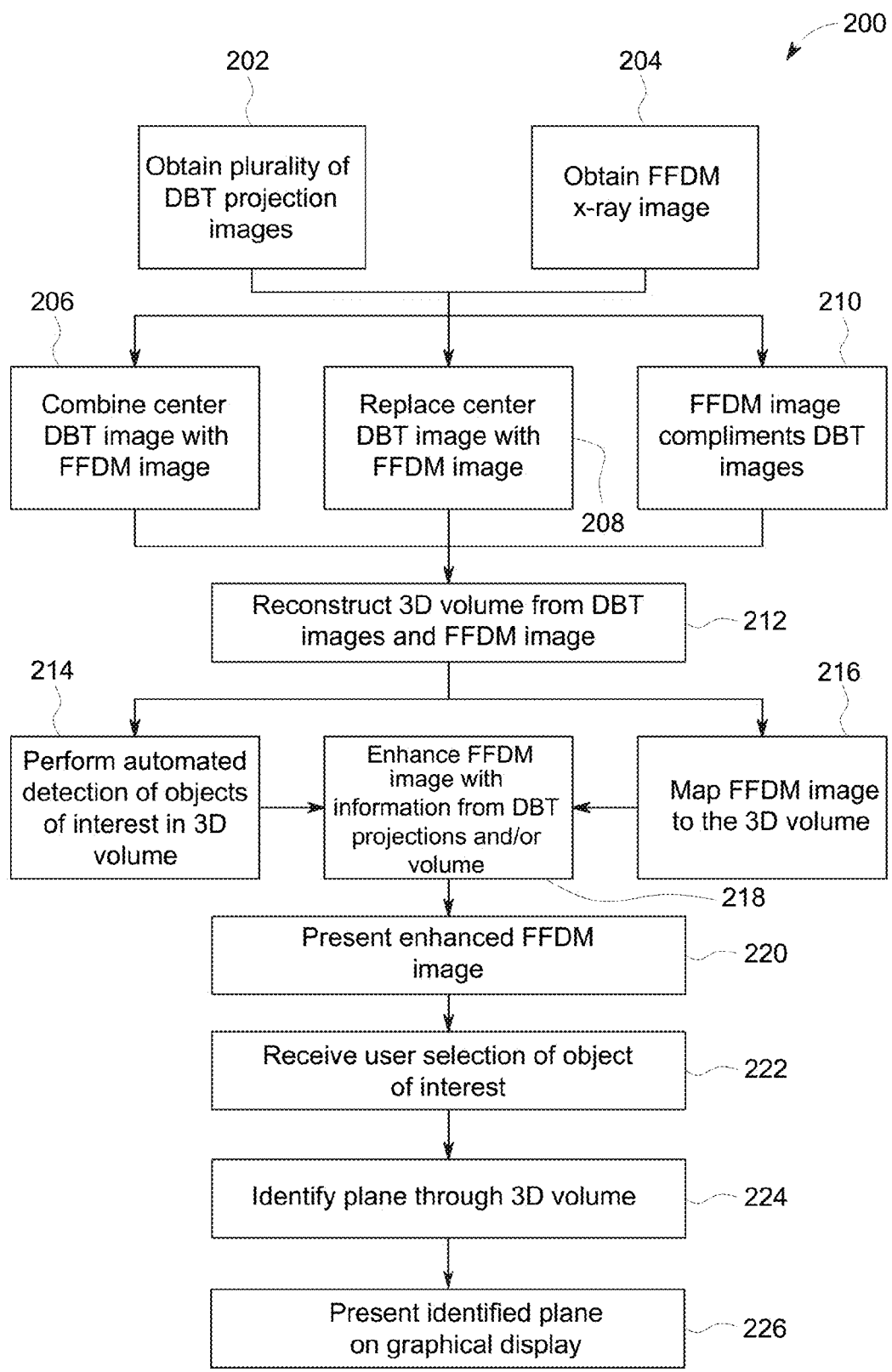
FIG. 5 is a flow chart depicting a more detailed exemplary embodiment of a method of imaging an organ of a patient.

FIG. 5 depicts a still further exemplary embodiment of a method 200 of imaging an organ of a patient. The method 200 begins with obtaining a plurality of DBT projection images at a first energy level at 202 and obtaining an FFDM image at a second energy level at 204. As described above, the obtained DBT projection images and FFDM image may be combined for a 3D reconstruction in a variety of ways. In each of these options the FFDM image is considered to have been acquired at a position orthogonal to the organ to be imaged, for example at 0° of rotation, while the plurality of DBT projection images are acquired at a plurality of angles relative to the orthogonal. It will be recognized that while the exemplary embodiments disclosed herein use an FFDM image acquired orthogonal to the object, the FFDM image may be acquired at another angle while remaining within the scope of the present disclosure.

At 206 the DBT projection image includes a center or orthogonal image. The center DBT image is combined with the FFDM image before reconstruction. At 208 the center DBT image is replaced with the FFDM image for 3D reconstruction. At 210 the FFDM image compliments the DBT images for example, the plurality of DBT projection images does not include a central or orthogonal image and therefore, the FFDM image is acquired instead of the center DBT image. Thus in exemplary embodiments, prior to reconstruction of the 3D volume, the FFDM x-ray image is added to the set of 2D projection images, for example in any of the techniques as described above. Then as described in further detail herein, a 3D volume and a synthetic 2D image may be created from the combination of the FFDM image and the set of 2D projection images.

At 212 a 3D volume is reconstructed from the DBT projection images and the FFDM image. Before reconstruction of the 3D volume, optionally a dynamic range correction factor is applied to at least one of the DBT images and/or the FFDM image. Since the plurality of DBT projection images and the FFDM image are acquired at different X-ray energy levels, in embodiments it is necessary to apply a dynamic range correction factor to one or both of the DBT projection images or the FFDM image.

Returning to 212 the 3D volume is reconstructed from the DBT images and the FFDM image using any of a variety of known reconstruction techniques, including filtered back projection reconstruction or iterative reconstruction techniques. In a still further exemplary embodiment, a modified filtered projection reconstruction technique may be used wherein greater weight is given to the FFDM image in the reconstruction over the contributions of the plurality of DBT projection images.

At 218, the FFDM image is enhanced with pixel information from the 2D projection images. For each pixel (i,j) of the FFDM image and for a given height, the algorithm accumulates the values of the corresponding pixel position in at least one of the tomosynthesis projections. A ranking of the accumulated values for each pixel over all possible heights is performed. The most likely height for each pixel (i,j) by selecting the maximum accumulated value is determined. The most likely height in each pixel (i,j) provides the navigational map. Each FFDM pixel (i,j)'s level is combined with the determined maximum values.

At 216 the FFDM image is mapped to the reconstructed 3D volume, creating a navigational map between the reconstructed 3D volume and the FFDM image. As explained above, since the organ is under the same compression for both the plurality of DBT projection images and the FFDM image, a synthetic 2D image of the 3D reconstructed volume from the position orthogonal to the organ corresponds to the FFDM image. In creating such a synthetic 2D image, the relationship of the features in that image to the 3D reconstructed volume is mapped and can be similarly used for the FFDM image.

In an exemplary embodiment, the synthetic 2D image is obtained by enhancing the FFDM image with information extracted from the 3D volume and combined into the FFDM image. As noted above, reconstructed 3D volumes, in some cases may exhibit improved detection of lesions, therefore the FFDM image may be enhanced to form a synthetic 2D image by detecting and extracting lesion information from the reconstructed 3D volume and combining this information with the FFDM image. In an exemplary embodiment, at 214, a computer aided diagnosis (CAD) software or program may automatically detect lesions and/or other areas of the 3D volume to extract and combine onto the FFDM image to create the synthetic 2D image. In another exemplary embodiment, a clinician may review the reconstructed 3D volume and may input or select region(s) or area(s) of the reconstructed 3D volume to extract and combine with the FFDM image to create the synthetic 2D image. In exemplary embodiments, the extracted information from the reconstructed 3D volume may be combined with the FFDM image for example by blending, superposition, mathematical combination, or other techniques as may be recognized by a person of ordinary skill in the art in view of the present disclosure. The navigational map is modified to include the z-position of the extracted areas at the corresponding (x,y) location in the FFDM image. A transformation involving a magnification factor might be required to compute the (x,y) position from the volume to the FFDM image.

At 214, Automated detection of objects of interest in the reconstructed 3D volume may be performed. This automated detection can be performed by any variety of known computer aided diagnosis (CAD) system or techniques. This identifies any lesions in the 3D reconstructed volume, which as noted above provides higher quality of lesion detection over FFDM.

At 220 the FFDM image with the identified objects of interest are presented in a GUI on a graphical display. A user interacts with the GUI presenting the FFDM image to input a selection of an object of interest. The system receives this user selection of an object of interest in the FFDM image at 222.

Upon receiving a user selection of the object of interest in the FFDM image at 222, a plane (e.g. a tomographic slice) through the 3D volume and the selected object of interest is identified at 224. The navigational map relates the location of the selected pixel of the selected object of interest in the 3D volume. In an exemplary embodiment, the system determines a center of the object of interest and identifies a tomographic slice through the center of the object of interest. In a still further embodiment, the thickness of the tomographic slice may be a fixed amount, may be selectable by the user, or may be automatically determined based upon a size of the selected object of interest.

Once the plane through the 3D volume is identified at 224, the tomographic slice is presented at 226 in the GUI on the graphical display. The user is able to further investigate the object of interest by reference to the tomographic slice and if the user wishes to investigate another object of interest the user inputs a new selection of an object of interest to the system and a new tomographic slice of the 3D volume and the selected object of interest is generated and presented on the graphical display.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram.

Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of imaging an organ of a patient, the method comprising:
   obtaining a plurality of two-dimensional (2D) tomosynthesis projection images of the organ by rotating an x-ray emitter to a plurality of orientations relative to the organ and emitting a first level of x-ray energization from the emitter for each projection image of the plurality of projection images;
   obtaining an x-ray image of the organ with a second level of x-ray energization
   reconstructing a three-dimensional (3D) volume of the organ from the plurality of tomosynthesis projection images and the x-ray image; and
   generating a synthetic 2D image of the organ from the plurality of tomosynthesis projection images and the x-ray image.

2. The method of claim 1 wherein the x-ray image is registered to fit in the tomosynthesis geometry.

3. The method of claim 1, wherein the plurality of 2D tomosynthesis projection images of the organ and the x-ray image of the organ are obtained during a same compression of the organ.

4. The method of claim 1, wherein the plurality of 2D tomosynthesis projection images and the x-ray image are further obtained with a detector that receives x-rays emitted from the x-ray emitter and further comprising:
   applying a dynamic range correction factor to at least one of either the plurality of 2D projection images or the x-ray image.

5. The method of claim 1, wherein the x-ray image is included to the set of 2D projection images prior to reconstructing the 3D volume and the synthetic 2D image.

6. The method of claim 1, wherein one of the plurality of 2D projection images is replaced by the x-ray image prior to reconstructing the 3D volume and the synthetic 2D image.

7. The method of claim 1, wherein one of the plurality of 2D projection images is combined with the x-ray image prior to reconstructing the 3D volume and the synthetic 2D image.

8. The method of claim 1, wherein the synthetic 2D image is obtained by enhancing the x-ray image using at least a subset of the plurality of 2D projection images or reconstructed slices.

9. The method of claim 1 further comprising:
   mapping the x-ray image to the 3D volume;
   presenting the x-ray or synthetic 2D image in a graphical user interface (GUI) presented on a graphical display;
   receiving a user selection of an object of interest in the x-ray image;
   identifying a plane through the 3D volume; and
   presenting the identified plane on the graphical display.

10. The method of claim 9, further comprising:
    extracting areas of the 3D volume; and
    enhancing the x-ray image or the synthetic 2D image with the areas extracted from the 3D volume
    enriching the mapping of the x-ray image or of the Synthetic 2D image to the 3D volume with the location of the extracted areas.

11. The method of claim 9, wherein mapping the x-ray image to the 3D volume comprises generating a navigation map containing height information from each pixel and obtained from the synthetic 2D generation process or from a reprojection operation of the 3D volume.

12. The method of claim 11 wherein the navigation map is stored into a DICOM header of the x-ray image and the synthetic 2D image.

13. A method of imaging an organ of a patient, the method comprising:
    obtaining a plurality of two-dimensional (2D) tomosynthesis projection images of the organ by rotating an x-ray emitter to a plurality of orientations relative to the organ and emitting a first level of x-ray energization from the emitter for each projection image of the plurality of projection images;
    obtaining an x-ray image of the organ with a second level of x-ray energization;
    reconstructing a three-dimensional (3D) volume of the organ from the plurality of tomosynthesis projection images;
    mapping the x-ray image to the 3D volume;
    presenting the x-ray image in a graphical user interface (GUI) presented on a graphical display;
    receiving a user selection of an object of interest in the x-ray image;
    identifying a plane through the 3D volume; and
    presenting the identified plane on the graphical display.

14. The method of claim 13 wherein the x-ray image is registered to fit in the tomosynthesis geometry.

15. The method of claim 13, wherein the plurality of 2D tomosynthesis projection images of the organ and the x-ray image of the organ are obtained during a same compression of the organ.

16. The method of claim 13, further comprising:
    extracting areas of the 3D volume; and
    enhancing the x-ray image with the areas extracted from the 3D volume
    enriching the mapping the x-ray image to the 3D volume with the location of the extracted areas.

17. The method of claim 13, wherein mapping the x-ray image to the 3D volume comprises generating a navigation map containing height information from each pixel and obtained from a synthetic 2D generation process or a reprojection operation of the 3D volume.

18. The method of claim 17, further comprising blending the synthetic 2D image with the x-ray image.

19. The method of claim 17 wherein the navigation map is stored into a DICOM header of the x-ray image.

20. A system of medical imaging, the system comprising:
    an x-ray emitter capable of producing x-rays at a first energization level and a second energization level, the x-ray emitter being rotatable to a plurality of orientations;
    an x-ray detector in at least partial alignment with the x-ray emitter;
    a processor operably connected to the x-ray emitter and the x-ray detector, the processor operates the x-ray emitter and detector to rotate about an organ to be imaged and obtain a plurality of two-dimensional (2D) projection images of the organ and the processor operates the x-ray emitter and detector to acquire an x-ray image of the organ at the second energization level; and a graphical display operably connected to the processor, the graphical display operated by the processor to present the x-ray image of the organ in a graphical user interface (GUI) presented on the graphical display;

wherein the processor reconstructs a three-dimensional (3D) volume of the organ from the plurality of projection images and maps the x-ray image to the 3D volume, and upon receiving a user selection of an object of interest in the x-ray image presented in the GUI on the graphical display, the processor identifies a plane through the 3D volume based upon a map of the x-ray image to the 3D volume and operates the graphical display to presented the identified plane.

21. The system of claim 20, the x-ray image is obtained with the x-ray emitter at an orthogonal orientation to the detector.

22. The system of claim 21, wherein an energization level of the emitter producing the x-rays decreases from the second level to the first level as the emitter rotates away from the orthogonal orientation to the detector.

23. The system of claim 20, wherein the processor reconstructs the 3D volume and a synthetic 2D representation of the organ from the plurality of projection images and the x-ray image.

24. The system of claim 23, wherein the processor automatically detects objects of interest in the 3D volume of the organ, and the x-ray image or the synthetic 2D image is enhanced with the detected objects of interest in the 3D volume of the organ.

25. The system of claim 23, wherein the processor reconstructs the 3D volume of the organ from the plurality of tomosynthesis projection images and the x-ray image using a filtered back projection reconstruction technique that gives particular weight to the x-ray image in the reconstruction.

26. The system of claim 20, wherein the processor applies a dynamic range correction factor to at least one of either the plurality of 2D projection images or the x-ray image.

27. The system of claim 20, wherein the system is a mammography system, the organ is a breast, and the x-ray image of the organ is a full field digital mammography (FFDM) image.

* * * * *